(12) United States Patent
Winkelmann

(10) Patent No.: US 12,004,930 B2
(45) Date of Patent: Jun. 11, 2024

(54) FIXED FLAT CLOTH DIAPER

(71) Applicant: Blythe Winkelmann, Elbert, CO (US)

(72) Inventor: Blythe Winkelmann, Elbert, CO (US)

( * ) Notice: Subject to any disclaimer, the term of this patent is extended or adjusted under 35 U.S.C. 154(b) by 87 days.

(21) Appl. No.: 17/349,115

(22) Filed: Jun. 16, 2021

(65) Prior Publication Data

US 2021/0386597 A1 Dec. 16, 2021

Related U.S. Application Data

(60) Provisional application No. 62/705,220, filed on Jun. 16, 2020.

(51) Int. Cl.
| | |
|---|---|
| *A61F 13/49* | (2006.01) |
| *A61F 13/496* | (2006.01) |
| *A61F 13/511* | (2006.01) |
| *A61F 13/514* | (2006.01) |
| *A61F 13/515* | (2006.01) |
| *A61F 13/538* | (2006.01) |
| *A61F 13/539* | (2006.01) |

(52) U.S. Cl.
CPC .... *A61F 13/49003* (2013.01); *A61F 13/4963* (2013.01); *A61F 13/5116* (2013.01); *A61F 13/51464* (2013.01); *A61F 13/515* (2013.01); *A61F 13/538* (2013.01); *A61F 13/539* (2013.01); *A61F 2013/49069* (2013.01); *A61F 2013/49071* (2013.01); *A61F 2013/49073* (2013.01); *A61F 2013/51139* (2013.01); *A61F 2013/51441* (2013.01); *A61F 2013/53966* (2013.01)

(58) Field of Classification Search
CPC ...... A61F 13/49003; A61F 2013/19069; A61F 2013/49071; A61F 2013/49073; A61F 13/49; A61F 13/505
See application file for complete search history.

(56) References Cited

U.S. PATENT DOCUMENTS 2,684,677 A * 7/1954 Pinney .............. A61F 13/49003
604/385.15
2,743,725 A * 5/1956 Matthews ......... A61F 13/49004
604/392

(Continued)

FOREIGN PATENT DOCUMENTS

DE 202017005841 U1 * 1/2018
FR 1304342 A * 9/1962
KR 200370196 Y1 * 12/2004

*Primary Examiner* — Guy K Townsend
*Assistant Examiner* — Peter Daniel Smith
(74) *Attorney, Agent, or Firm* — AVEK IP, LLC

(57) ABSTRACT

The diaper of the present invention is a fixed flat cloth diaper. The diaper is 'fixed', because an outer layer of the diaper resembles the final format of a flat, rectangular cloth diaper having been folded origami style into a shape suitable for donning on a wearer by a user. The outer layer functions primarily to retain the diaper upon the wearer and has a stomach panel for obtaining a good closure of the diaper on the wearer. The diaper is 'flat', because an inner layer of the diaper is attached to the outer layer, and the inner layer is a flat, rectangular shape which is customizable for absorbency and can be folded into a flat insert configuration of the user's choice prior to donning the diaper on the wearer. The inner layer functions primarily to absorb waste (urine and feces) excreted by the wearer.

1 Claim, 5 Drawing Sheets

(56) References Cited

U.S. PATENT DOCUMENTS

| | | | |
|---|---|---|---|
| 3,368,562 A * | 2/1968 | Vogt | A61F 13/49004 |
| | | | 604/385.201 |
| 8,079,996 B2 | 12/2011 | Yang | |
| 8,115,050 B2 | 2/2012 | Ormbsby et al. | |
| 8,425,483 B2 | 4/2013 | Ekstrom | |
| 8,734,419 B2 | 5/2014 | Ormsby | |
| 8,961,484 B1 | 2/2015 | Ekstrom | |
| 9,138,358 B2 * | 9/2015 | Catoe | A61F 13/15268 |
| 9,387,138 B2 * | 7/2016 | Roe | A61F 13/5633 |
| 9,572,726 B1 | 2/2017 | Ekstrom | |
| 10,201,460 B1 | 2/2019 | Ekstrom | |
| 10,258,514 B2 | 4/2019 | Wojtanowski | |
| 10,327,962 B2 | 6/2019 | Bryan et al. | |
| 2008/0215028 A1 | 9/2008 | Brown et al. | |
| 2014/0296820 A1 | 10/2014 | Malone | |
| 2016/0058631 A1 | 3/2016 | Ormsby | |
| 2021/0290447 A1 * | 9/2021 | Sepello | A61F 13/15268 |

\* cited by examiner

FIXED FLAT CLOTH DIAPER

CROSS-REFERENCE TO RELATED APPLICATION

This application claims the benefit of priority under 35 U.S.C. § 119(e) from U.S. Provisional Application Ser. No. 62/705,220, filed Jun. 16, 2020, titled "Blythe Life "Fixed" Flat Cloth Diaper," and the entire contents of which are incorporated by reference herein, and should be considered a part of this specification.

BACKGROUND OF THE INVENTION

Field of the Invention

The field of the invention generally relates to cloth diapers, and in particular is a fixed flat cloth diaper.

Description of Related Art Including Information Disclosed Under 37 CFR 1.97 and 37 CFR 1.98

Cloth diapers are known and have many variations. These variations include the traditional cloth diaper consisting of a rectangular cloth having a longitudinal center section for absorbing wearer waste (urine and feces), which section may be a thick layer or multiple layers of absorbent cloth or fabric. There are other more relatively recent cloth diaper variations.

A contour diaper is a fitted diaper, hourglass in shape, may or may not have elastic in the leg area to create a leg seal (but usually does not), does not require any folding to achieve a fit, has a very distinct narrow contour at the middle of the diaper that goes up and over the crotch area of the wearer, omitting all excess fabric, which fits right between the legs of the wearer, and must have a cover with elastic legs to achieve a leg seal on a wearer, such as an infant, baby, or child. Contour diapers are not fitted at the legs or waist and need to be secured with diaper pins, Snappi® brand teethed fasteners for use with cloth diapers, or with a wrap-styled diaper cover by a user of the diaper upon the wearer of the diaper. Contour diapers have a trimmer fit in the crotch compared to a pre-fold cloth diaper, but still provide adequate absorbency where most needed for the wearer by means of a snake or regular booster sewn into the middle to add absorbency, or may be sewn into the top of the diaper, like a flap of cloth that can be folded downward into the interior of the diaper. Contour diapers are simple in design allowing for adjustability in the rise, such as by means of a fold-down rise, and dry quickly. Contour diapers are an economical alternative to fitted diapers and are fairly easy to use by the user.

An all-in-one cloth diaper consists of a waterproof cover layer with a sewn-in cloth layer for absorbency. The all-in-one cloth diaper requires no user assembly prior to use, and is most similar to a disposable diaper.

An all-in-two cloth diaper consists of a waterproof cover layer with a snap-in cloth layer for absorbency. The snap-in cloth layer can be removed for washing or switching out snap-in cloth layer inserts for multiple re-uses of the cover layer.

A fitted or hybrid fitted cloth diaper is typically an absorbent cloth layer without a waterproof cover layer, such as the all-in-one and all-in-two cloth diapers. Some fitted cloth diapers have either a concealed waterproof inner layer, or a waterproof cover layer on the outside, and, thus, these cloth diapers are referred to as a hybrid fitted cloth diaper. In contrast, for a regular fitted cloth diaper, an extra waterproof outer cover is needed. With a hybrid fitted cloth diaper that includes a waterproof inner layer or waterproof cover layer, an extra waterproof outer cover is not needed.

A pocket cloth diaper consists of a waterproof outer cover with a stay dry liner that creates a pocket at the front side, back side, or both front and back sides of the diaper. The pocket of the diaper is stuffed with an absorbent material of the user's choice. Leg gussets on the pocket cloth diaper also provide a gentle, yet secure, leak protection leg seal on the wearer.

A pre-fold cloth diaper consists of multiple layers of absorbent fabric or cloth, which layers are all sewn together, and the diapers are rectangular or square in shape. The diapers can be wrapped and pinned around the wearer, or can be folded into a pad for use in covers or pockets of other cloth diaper variants.

Cloth diapers known as flat cloth diapers or stretchy flat cloth diapers consist of a rectangular or square piece of absorbent, non-stretchy or stretchy, fabric or cloth which can be folded in multiple ways to create the user's desired level of absorbency and fit needed for the wearer. For use, flats or stretchy flats cloth diapers are typically folded by the user into configurations prior to placing the diaper on the wearer. Common configurations are referred to as an origami fold, and as a kite fold.

A pre-flat cloth diaper consists of an intermediate combination between a flat or stretchy flat cloth diaper and a pre-fold cloth diaper. The pre-flat cloth diaper consists of a pre-fold cloth diaper with 'wings' added to the basic shape and which wings enable the diaper to be wrapped and pinned more securely on the wearer by the user.

U.S. Pat. No. 8,079,996 issued Dec. 20, 2011, by Yang for "Cloth Diaper the Size of Which Is Adjustable" discloses a cloth diaper the size of which is adjustable and that is mainly made up with a surface layer cloth and a liner layer cloth and is provided with a waistline section. The cloth diaper further includes an adjusting unit provided with two buckling parts, and an adjusting surface opposite to the buckling parts. Thus, to adjust the cloth diaper to a determined size, only each of the buckling parts of the adjusting unit is buckled and fixed onto the adjusting surface to form a cloth diaper the size of which is properly adjustable. Thus, following the child and infant's figure, the cloth diaper may be adjusted randomly.

U.S. Pat. No. 8,115,050 issued Feb. 14, 2012, by Ormsby et al. for "Soaker Pad for Cloth Diaper" discloses a soaker pad for a cloth diaper comprising an outer layer, absorbent pad, inner layer, and side panels. The inner longitudinal edge of each side panel is folded inward to create a fold line and fold area. Elastics are located just inside the fold line to create an inner gusset. Elastics are situated parallel to the longitudinal edge of the outer layer to create an outer gusset. Neither the inner nor outer gusset is in contact with the inner layer. Each side panel is adhered to the outer layer in the margin along each longitudinal edge of the outer layer that is not in contact with the inner layer and along the outer margins of the inner layer. The fold area is adhered to the inner layer except at the middle portion of the fold area, thereby allowing the inner gusset to stand up and away from the inner layer.

U.S. Pat. No. 8,425,483 issued Apr. 23, 2013, by Ekstrom for "Double Gusset Cloth Diaper Along with Method for Making the Same" discloses a double gusset cloth diaper including an inner surface and an outer surface forming an hourglass shape, having a groin area proximate a center line of the reusable diaper and defining at least one recess therebetween. A fluid absorbent material is removably located in the recess through the opening. A first gusset is attached to the reusable diaper to form a first seal between the inner surface and the legs of the user. A second gusset is attached to the reusable diaper proximate the first gusset. The gussets are formed of an elastic material attached to the wrong side of the inner surface in a channel formed by stitching the inner surface to form channels.

U.S. Pat. No. 8,734,419 issued May 27, 2014, by Ormsby for "Cloth Training Diaper" discloses a cloth training diaper comprising an outer layer coupled to an inner layer, a front portion and a rear portion, a plurality of snaps arranged longitudinally along the right side of the front portion, the left side of the front portion, the right side of the rear portion, and the left side of the rear portion, the snaps extending through the outer and inner layers, and two side panels, each side panel comprised of a smocked material coupled to a non-smocked material, each side panel having a right side and a left side and a plurality of snaps arranged along the right and left sides of the smocked material. The snaps on the side panels engage with the snaps on the front and rear portions.

U.S. Pat. No. 8,961,484 issued Feb. 24, 2015, by Ekstrom for "Double Gusset Cloth Diaper Along with Method for Making the Same" discloses a double gusset cloth diaper including an inner surface and an outer surface forming an hourglass shape, having a groin area proximate a center line of the reusable diaper and defining at least one recess therebetween. A fluid absorbent material is removably located in the recess through the opening. A first gusset is attached to the reusable diaper to form a first seal between the inner surface and the legs of the user. A second gusset is attached to the reusable diaper proximate the first gusset. The gussets are formed of an elastic material attached to the wrong side of the inner surface in a channel formed by stitching the inner surface to form channels.

U.S. Pat. No. 9,138,358 issued Sep. 22, 2015, by Catoe for "Cloth Diaper" discloses a reusable, cloth diaper of singular construction. The diaper is generally shaped like a classic hourglass configuration, and includes a pair of absorbent flaps in a cross-flap configuration on an inner portion thereof, wherein one flap is attached to a rear portion of the diaper and the other flap is attached to a front portion of the diaper, each adjacent to the child's waist. The outer layer of the diaper is preferably made from a blend of bamboo and cotton, and includes a polyurethane laminate layer on the inner surface of the outer layer. The diaper construction further includes means for adjusting waist and crotch sizes, as well as storage snap means for securing the diaper into a rolled up storage and transport configuration.

U.S. Pat. No. 9,572,726 issued Feb. 21, 2017, by Ekstrom for "Double Gusset Cloth Diaper Along with Method for Making the Same" discloses a double gusset cloth diaper including an inner surface and an outer surface forming an hourglass shape, having a groin area proximate a center line of the reusable diaper and defining at least one recess therebetween. A fluid absorbent material is removably located in the recess through the opening. A first gusset is attached to the reusable diaper to form a first seal between the inner surface and the legs of the user. A second gusset is attached to the reusable diaper proximate the first gusset. The gussets are formed of an elastic material attached to the wrong side of the inner surface in a channel formed by stitching the inner surface to form channels.

U.S. Pat. No. 10,201,460 issued Feb. 12, 2019, by Ekstrom for "Double Gusset Cloth Diaper Along with Method for Making the Same" discloses a double gusset cloth diaper including an inner surface and an outer surface forming an hourglass shape, having a groin area proximate a center line of the reusable diaper and defining at least one recess therebetween. A fluid absorbent material is removably located in the recess through the opening. A first gusset is attached to the reusable diaper to form a first seal between the inner surface and the legs of the user. A second gusset is attached to the reusable diaper proximate the first gusset. The gussets are formed of an elastic material attached to the wrong side of the inner surface in a channel formed by stitching the inner surface to form channels.

U.S. Pat. No. 10,258,514 issued Apr. 16, 2019, by Wojtanowski for "Reusable Cloth Diapers That Can Be Closed Shut When Soiled to Contain Wastes with a Thin Insert That Can Absorb a Defined Amount, Is Contoured, and Can Easily Be Guided into a Diaper" discloses reusable cloth diapers. In the diaper is an insert in which there are inner absorbing layers that are arranged specifically to absorb and hold a predetermined volume of waste. Also, the layers are sewn on three sides leaving a pocket opening that allows a person to easily guide their hand into the insert to easily guide and place into position inside the reusable cloth diaper.

U.S. Pat. No. 10,327,962 issued Jun. 25, 2019, by Bryan et al. for "Cloth Diaper with Adjustment Features" discloses systems and methods for an adjustable reusable diaper. Some systems include a reusable diaper including a sealing apparatus configured to keep fluid sealed within the diaper. The sealing apparatus may include one or more elastic members and one or more gussets where one elastic member is threaded through channels of the one or more gussets. Some systems include a reusable diaper and one or more soaker pads configured to be attachable to the reusable diaper. The soaker pads may be of varying sizes and shapes and can be selectively attached to the reusable diaper to effect different absorption volumes and patterns within the diaper. The soaker pads may be received in one or more pockets of the reusable diaper. Some systems include one or more openings to a pocket to allow a user to more efficiently attach and position one or more soaker pads in a reusable diaper.

US Patent Publication 2008/021528 published Sep. 4, 2008, by Brown et al. for "Highly-Adjustable, Fitted Cloth Diaper" discloses a cloth diaper that is fitted, washable and reusable, and highly effective in reducing or preventing leaks. The diaper comprises fabric preferably on both the outermost surface and the inner most surface that is stretchable, soft, and has hydrophilic and wicking properties. The diaper comprises an inner absorbent layer(s) between said hydrophilic and wicking fabric layers. A preferred continuously-adjustable fastening system may be used to adapt the diaper to fit a wide range of sizes of infants and toddlers, for example, from birth up to four years old. The fastening system allows a large amount of the front side of the diaper to be folded inside the diaper, significantly changing the overall size of the diaper to accommodate small infants. Even with the large folded-in flap, soft, wicking fabric is maintained against the child's skin, and the fastener system portion that is also folded inward does not interfere with absorbency. The preferred "V-shaped" fastener extends far down on the front side of the diaper, most of the way to the "crotch" area of the diaper, and also has wings/extensions from the top ends of the arms of the "V", thus, allowing fastening of the diaper all along the length of each of the arms of the "V" and also out along the transverse length of the wing/extensions.

US Patent Publication 2014/0296820 published Oct. 2, 2014, by Malone for "Cloth Diaper" discloses a cloth diaper that includes a size adjustable impermeable outer layer, and an elongated absorbent insert permanently attached only at one end to the inside of said outer layer, near the upper edge of the outer layer. The absorbent insert extends a substantial distance beyond the opposite upper edge of said outer layer. Preferably, there is an absorbent layer attached to the outer layer, between the outer layer and the insert.

US Patent Publication 2016/0058631 published Mar. 3, 2016, by Ormsby for "Cloth Diaper with Dual-Closure System" discloses a cloth diaper comprising a front panel, a plurality of snaps configured in a first row situated directly underneath the top edge of the front panel, a strip of hook-and-loop fastener material that snaps onto the plurality of snaps configured in a first row and situated directly underneath the top edge of the front panel, a rear panel, a first side wing comprising at least one snap on an inside surface of the first side wing, a second side wing comprising at least one snap on an inside surface of the second side wing, a first side wing hook-and-loop attachment member that snaps onto the at least one snap on the inside surface of the first side wing, and a second side wing hook-and-loop attachment member that snaps onto the at least one snap on the inside surface of the second side wing.

The known cloth diaper variations have disadvantages for the user and the wearer. Among these are that flat cloth diapers come unfolded easily, especially when the user is attempting to diaper a mobile, or squirming, child, or wearer. Diapers that need the use of a fastener, such as diaper pins, Snappi fasteners, or Boingo® brand catch fasteners for use with cloth diapers, can rub and scratch the wearer's hips if there is not a tummy panel for protection, or multiple layers of fabric on the wings of the diapers. Pre-fold, pre-flat, fitted, and all-in-one diapers usually have many layers sewn into the diaper. These types of diapers and booster inserts can be very thick due to the fabric and the layers used, and also make washing and drying potentially problematic without an excellent wash routine, because waste residues of ammonia (from urine) and minerals (from feces) can be retained in the fabric fibers. These diapers also take an extremely long amount of time to dry fully due to the multiple fabric layers many of them have.

Pre-folds and the mixed pre-flats do not allow for a tight or long-lasting leg seal on the wearer due to the diaper fabric bulk at the legs, crotch, and hips. These diapers are multiple layers that are all one piece which must be folded in from the sides often creating many layers of fabric along the seal line. Pre-folds are usually not made from a stretchy fabric and can be very stiff. The modern pre-flat or winged-flat can be stretchy, but again, must be folded multiple times to achieve the absorbency needed for any kind of wear-time. Some pre-flats come with only two layers of fabric, but typically are so thin and small in width that the wearer easily wets or soaks through the layers, and, thus, inserts and boosters must be added to achieve the absorbency needed.

Many diapers need multiple pieces for a complete diapering system for the amount of absorbency needed. Diapers that are considered for use with heavy-wetter wearers are bulky, and pose a difficulty to find covers and clothing to fit over them.

BRIEF SUMMARY OF THE INVENTION

A cloth diaper of the present invention comprises an outer layer having a main panel with a trapezoid shape with a left hip wing and a right hip wing, which hip wings are contiguous with each other, and a stomach panel with an ellipse shape with a left stomach wing and a right stomach wing, which stomach wings are contiguous with each other, and the main panel is contiguous along a shorter width of the trapezoid shape with the stomach panel; and an inner layer having a rectangle shape with a left absorbency panel and a right absorbency panel, which panels are contiguous with each other, and having a tab with an area above a tab line, and an attachment seam; wherein the tab of the inner layer is attached along the attachment seam to a corresponding portion of the outer layer.

The outer layer of the diaper of the present invention further comprises an outer layer seam allowance which seam allowance bounds a perimeter of the outer layer, and the inner layer of the diaper of the present invention further comprises an inner layer seam allowance which seam allowance bounds a perimeter of the inner layer. The outer layer comprises at least a layer of fabric finished along the seam allowance, and the inner layer comprises at least a layer of fabric finished along the seam allowance. Alternatively, in another embodiment, the outer layer comprises two layers of fabric, which layers of fabric are adjoined together as one piece and finished along the seam allowance. Alternatively, in another embodiment, the inner layer comprises two layers of fabric, which layers of fabric are adjoined together as one piece and finished along the seam allowance. Preferably, a direction of a fabric grain for the inner layer is aligned with and parallel to a center line of the inner layer.

The cloth diaper of the present invention preferably is constructed of a fabric having from about 3% to about 7% of synthetic, elastic fiber content, and the fabric used to construct the diaper is selected from the group consisting of stretch French terry, stretch fleece, and blends thereof. Preferably, the fabric is made of fibers selected from the group consisting of bamboo, cotton, organic cotton, hemp, soy, wool, Merino wool, lyocell, modal, and blends thereof.

Figure 1:
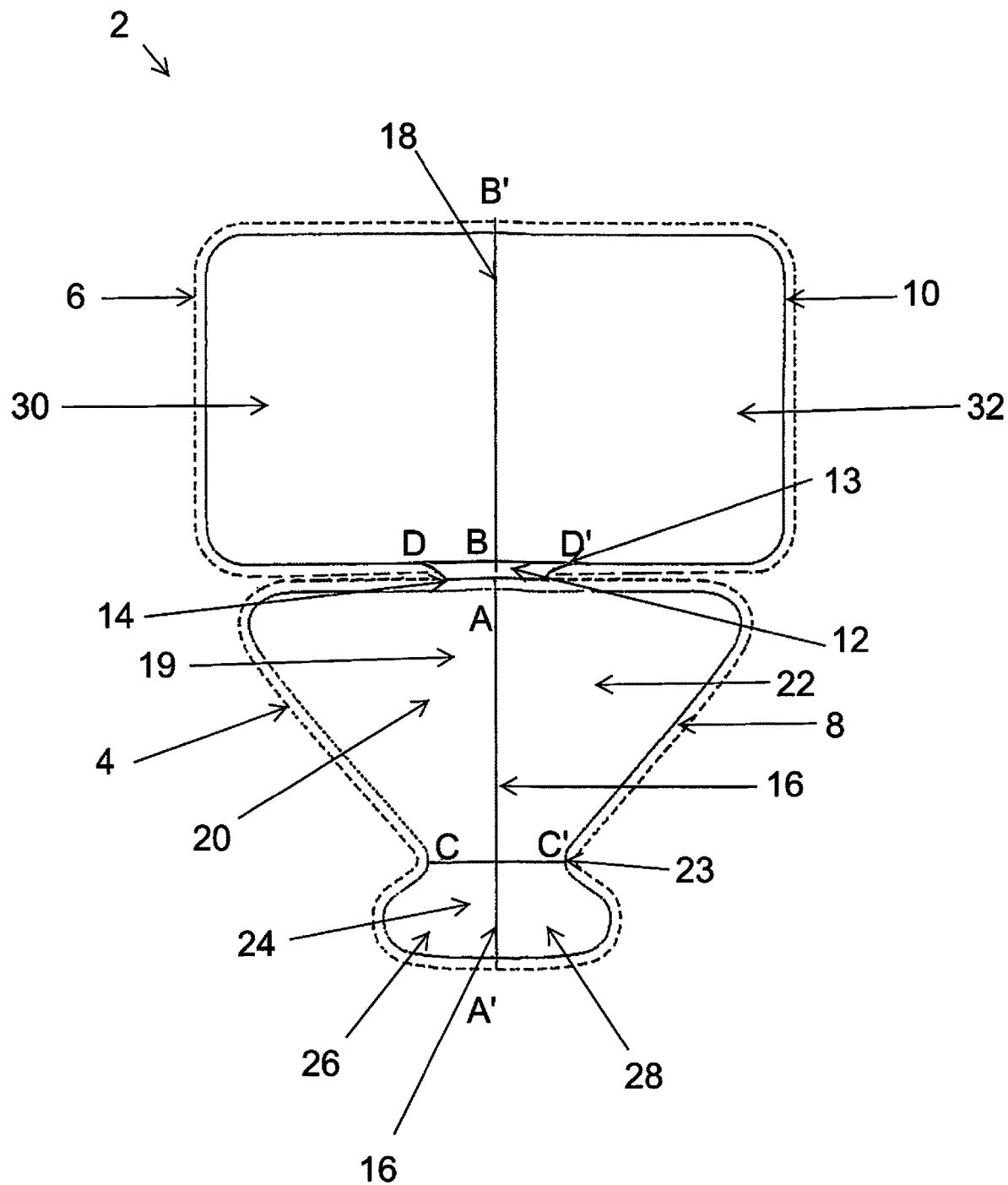
FIG. 1 is a top plan view of a cloth diaper of the present invention in an unfolded configuration.

LIST OF REFERENCE NUMERALS 2 diaper
4 outer layer
6 inner layer
8 outer layer seam allowance
10 inner layer seam allowance
12 inner layer tab
13 tab line D-D'
14 attachment seam
16 outer layer center line A-A'
18 inner layer center line B-B'
19 main panel
20 left hip wing
22 right hip wing 23 panel line C-C'
24 stomach panel
26 left stomach wing
28 right stomach wing
30 left absorbency panel
32 right absorbency panel

DETAILED DESCRIPTION OF THE INVENTION

The diaper of the present invention is a fixed flat cloth diaper. The diaper is 'fixed', because an outer layer of the diaper resembles the final format of a flat, rectangular cloth diaper having been folded origami style into a shape suitable for donning on a wearer by a user; wherein a wearer is a human newborn, infant, baby, child, or toddler. The outer layer functions primarily to retain the diaper upon the wearer. The diaper is 'flat', because an inner layer of the diaper is attached to the outer layer, and the inner layer is a flat, rectangular shape which is customizable and can be folded into a flat insert configuration of the user's choice prior to donning the diaper on the wearer. The inner layer functions primarily to absorb waste (urine and feces) excreted by the wearer.

The cloth diaper of the present invention requires little to no folding prior to or upon donning the diaper by the user on the wearer and the outer layer has a stomach panel for obtaining a good closure. The diaper of the present invention also has a flat insert inner layer which enables the user to obtain a customized absorbency for the wearer by folding the inner layer into any of numerous desired configurations.

The fixed flat cloth diaper of the present invention solves many issues posed by other cloth diapers. The diaper of the present invention does not become unfolded, as frequently happens with pre-fold, pre-flat, fitted, and all-in-one diapers. The diaper of the present invention washes well and dries quickly because it does not have multiple, thick layers, as compared to pre-fold, pre-flat, fitted, and all-in-one diapers which do. The diaper of the present invention also solves the issue of many pre-fold diapers and the mixed pre-flat diapers not allowing for a good leg seal due to cloth fabric bulk at the legs, crotch, and hips of the wearer.

Figure 2:
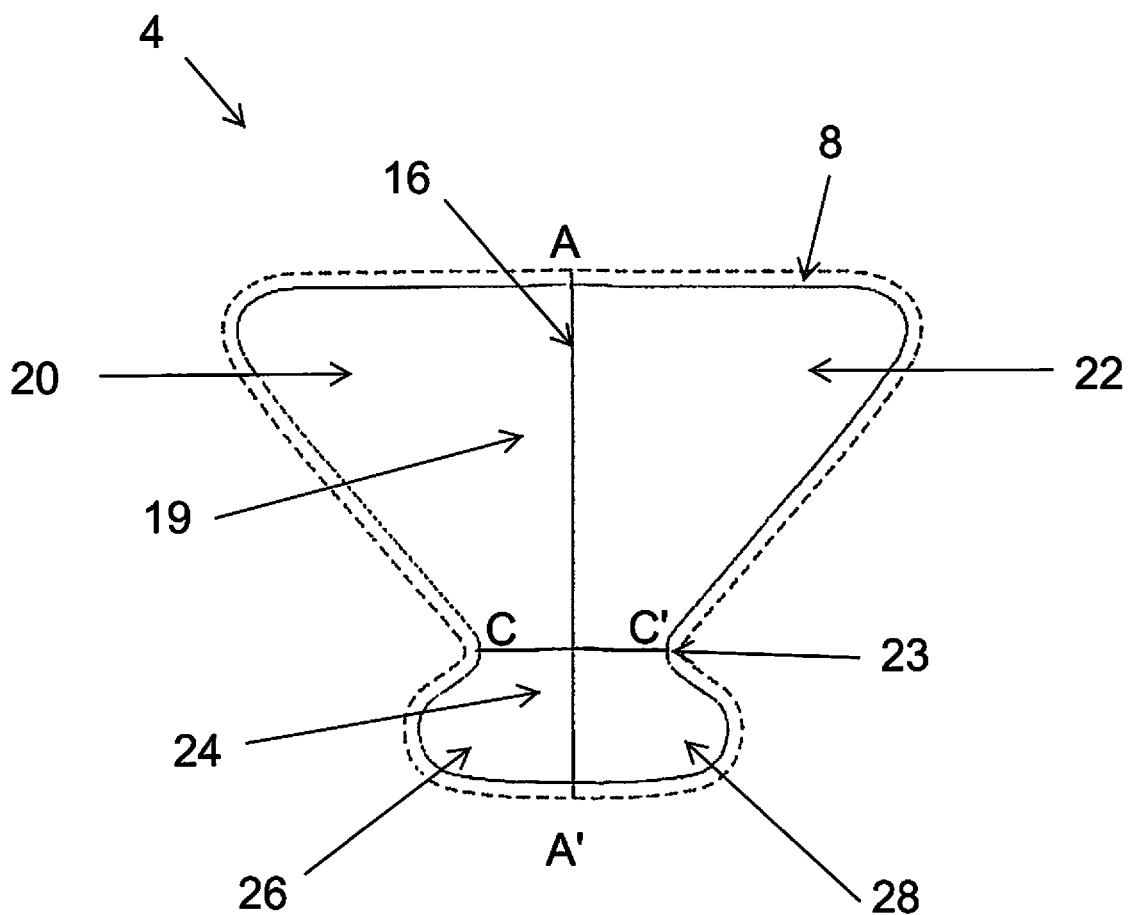
FIG. 2 is top plan view of an outer layer of the cloth diaper of the present invention.

With reference to FIG. 1 and FIG. 2, a diaper 2 of the present invention comprises an outer layer 4 having an overall shape resembling a modified obtuse triangle, and comprising a main panel 19, which main panel 19 is a trapezoid shape, and is contiguous along a shorter width of the trapezoid shape with a stomach panel 24, which stomach panel 24 is an ellipse in shape; wherein the main panel 19 is an area above a panel line C-C' 23, and the stomach panel is an area below the panel line C-C' 23. The main panel 19 comprises, from a user's perspective, a left hip wing 20 and a right hip wing 22; wherein the left hip wing 20 is an area to the left of an outer layer center line A-A' 16, and the right hip wing 22 is an area to the right of the outer layer center line A-A' 16. The stomach panel 24 comprises, from the user's perspective, a left stomach wing 26 and a right stomach wing 28; wherein the left stomach wing 26 is an area to the left of an outer layer center line A-A' 16, and the right stomach wing 28 is an area to the right of the outer layer center line A-A' 16. The outer layer 4 further comprises an outer layer seam allowance 8, which seam allowance 8 bounds a perimeter of the outer layer 4, and the seam allowance 8 is shown by and defined as an area between an outer dotted line and an inner solid line. The seam allowance 8 is from about 0.5" to about 1.0" in width, per user preference in construction, and parameters of an overlook sewing machine used to sew a serged seam or edge. The outer layer 4 is comprised of at least a layer of fabric, and finished along seam allowance 8. Alternatively, the outer layer 4 can be comprised of two layers of fabric, which layers are overlaid upon each other and adjoined together as one piece, and finished along seam allowance 8.

Figure 3:
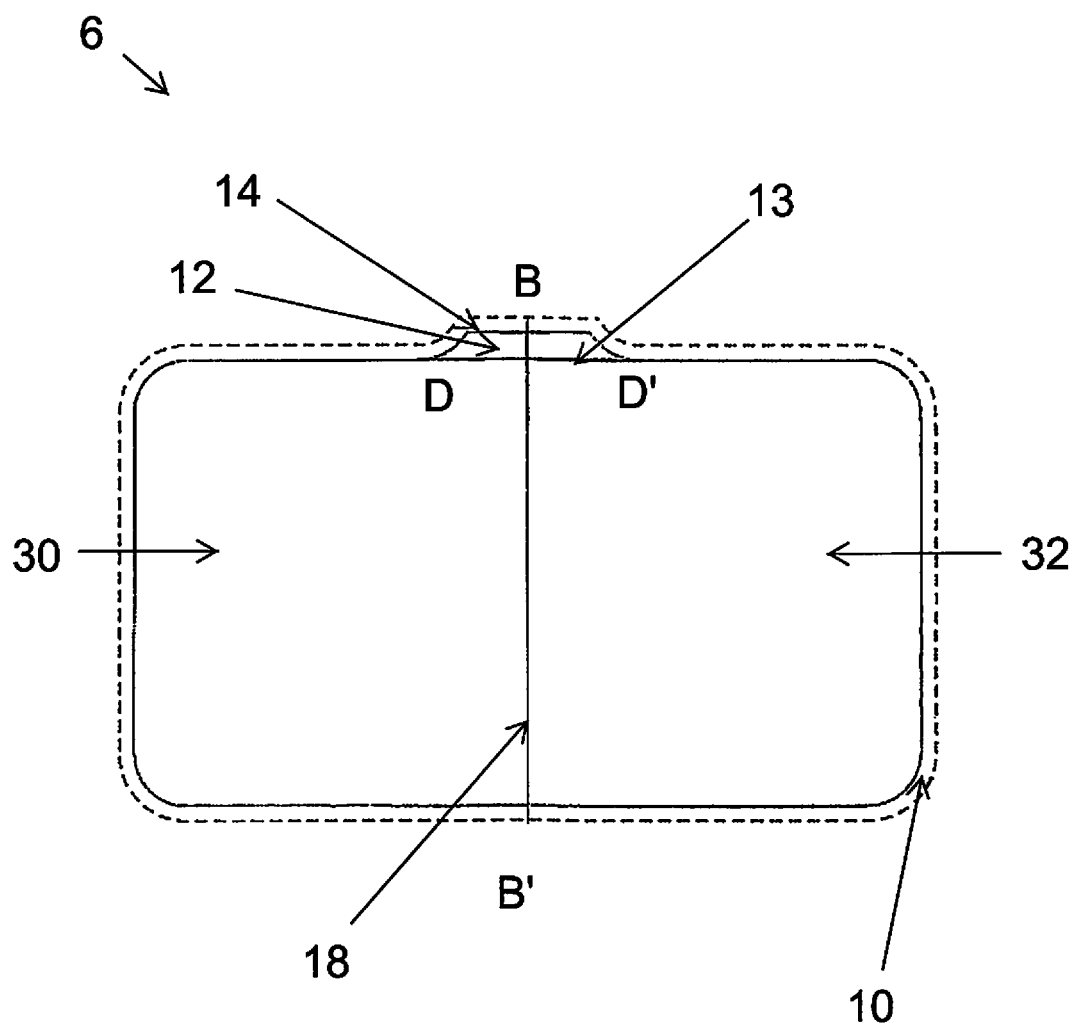
FIG. 3 is a top plan view of an inner layer of the cloth diaper of the present invention.

With reference to FIG. 1 and FIG. 3, the diaper 2 of the present invention further comprises an inner layer 6 having an overall shape resembling a rectangle, and comprising, from the user's perspective, a left absorbency panel 30 and a right absorbency panel 32; wherein the left absorbency panel 30 is an area to the left of an inner layer center line B-B' 18, and the right absorbency panel 32 is an area to the right of the inner layer center line B-B' 18. The inner layer 6 further comprises a tab 12; wherein the tab 12 is an area above a tab line D-D' 13, and the tab 12 is from about 3.0" to about 6.0" in width. The inner layer 6 further comprises an inner layer seam allowance 10, which seam allowance 10 bounds a perimeter of the inner layer 6 and the seam allowance 10 is shown by and defined as an area between an outer dotted line and an inner solid line. The seam allowance 10 is from about 0.5" to about 1.0" in width, per user preference in construction, and parameters of an overlook sewing machine used to sew a serged seam or edge.

Figure 4:
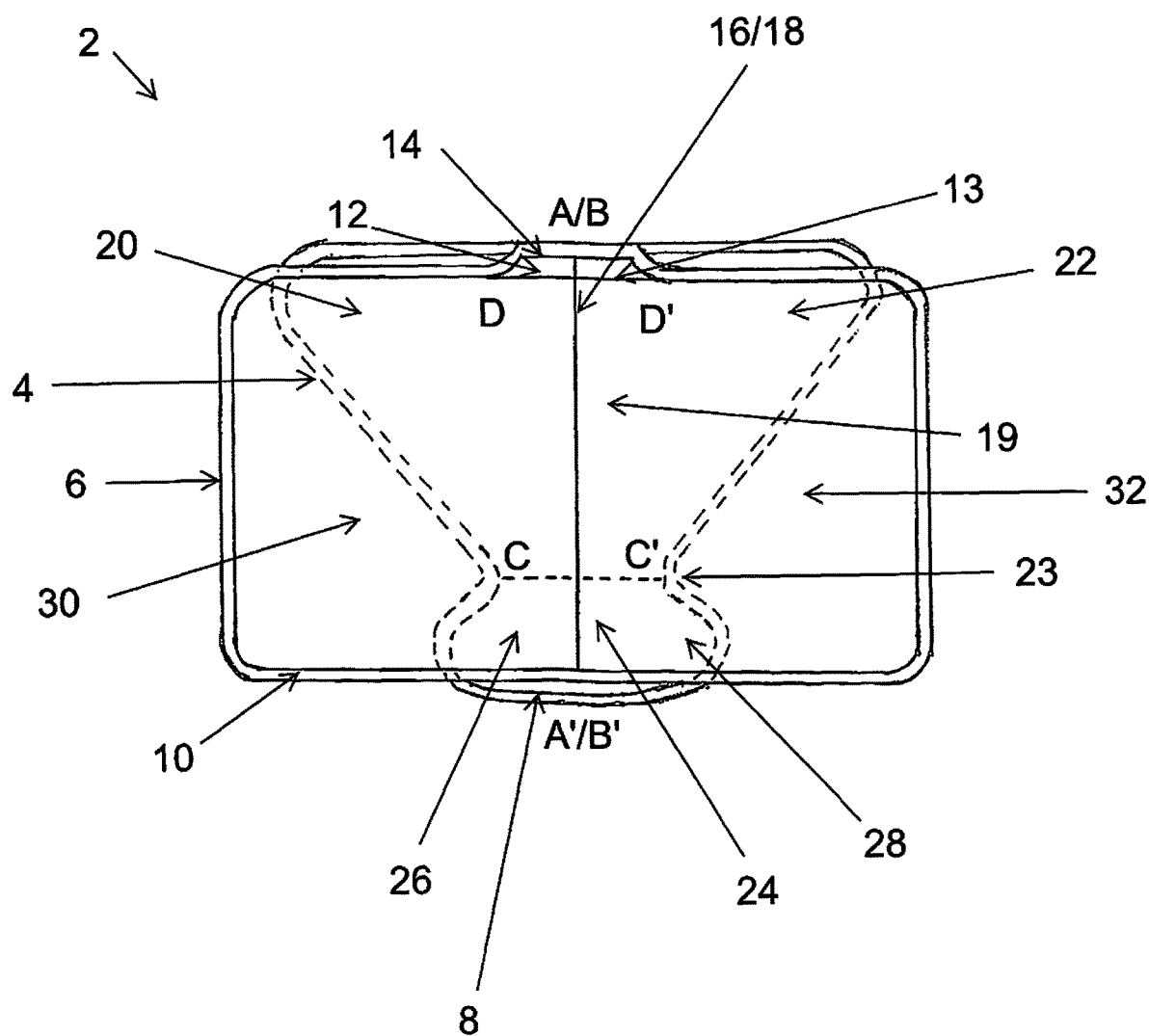
FIG. 4 is a top plan view of the cloth diaper of the present invention in an initial-fold configuration.

With reference to FIG. 1 and FIG. 4 the diaper 2 of the present invention further comprises attachment of the outer layer 4 to the inner layer 6. As shown on FIG. 4, to attach the inner layer 6 to the outer layer 4, a portion of the seam allowance 10 equivalent to an area of a minimal attachment seam 14 of the tab 12 is attached to a corresponding portion of the seam allowance 8 of the outer layer 4. The minimal attachment seam 14 is from about 3.0" to about 6.0" in length. The inner layer 6 is comprised of at least a layer of fabric. The inner layer can be comprised of a single layer of fabric, which is suitable for use with a regular wetter wearer, and finished along seam allowance 10; or can be comprised of two layers of fabric, suitable for use with a heavy wetter wearer, which layers are overlaid upon each other and adjoined together as one piece, and finished along seam allowance 10. Additionally, a two layer fabric inner layer 6 provides an effective absorbency solution without the need to add separate, absorbent inserts or boosters.

With reference to FIG. 4, the inner layer 6 of the diaper 2 is shown on top of, or folded over on, the outer layer 4 of the diaper 2. The portion of the outer layer 4 laying underneath the inner layer 6 is outlined by a portion of seam allowance 8, which portion of seam allowance 8 is shown by and defined as an area between an outer dotted line and an inner dotted line. Otherwise, as shown on FIG. 4, the portions of the outer layer 4 which do not lay underneath the inner layer 6, are outlined by another portion of seam allowance 8, which other portion of seam allowance 8 is shown by and defined as an area between an outer solid line and an inner solid line. Also as otherwise shown on FIG. 4, the inner layer 6 seam allowance 10 is shown by and defined as an area between an outer solid line and an inner solid line.

The diaper 2 of the present invention is preferably constructed of cloths or fabrics made with natural fibers and having a low percentage of synthetic, elastic fibers, such as spandex, Lycra®, or elastane, from about 3% to about 7%. Such fabrics are stretchy and enable the diaper 2 of the present invention, when in use upon a wearer, to achieve the best stretch, leg seal, and absorbency. Suitable, preferred fabrics for construction of the diaper 2 of the present invention are stretch French terry, stretch fleece, and blends thereof. Suitable, preferred fabrics are also made from natural fibers, such as bamboo, cotton, organic cotton, hemp, soy, wool, Merino wool, lyocell, Tencel®, and blends thereof. Many of these fabric blends have an anti-microbial property that naturally fights bacteria and fungus in the fabric. The fabric blends such as bamboo, lyocell, and wool have properties that assist in preventing microbes from developing while promoting moisture movement, which in turn, gives maximum wear comfort to the wearer. These fabrics provide a higher quality to the diaper 2 and boost sanitation due to the nature of any diaper being in constant contact with human waste. Additionally, these fabric blends, when wet, will not feel cold and clammy to the wearer, thus, making the fabric blends the preferred fabrics for construction of the diaper 2 of the present invention. Hemp fabric blends are highly absorbent and outperform most other fabrics or textiles. Additionally, when hemp is paired with bamboo, the absorbency and softness of the resultant fabric are well-suited for use as the inner layer 6 of the diaper 2. Organic cotton is quick-absorbing and is a great fiber addition to any fabric blend used, including organic cotton blended with bamboo, for the diaper 2 and is well-suited for use in the diaper 2 as used for wearers who heavily wet, or flood, the diaper 2. Although jersey knit fabrics can be used to construct the diaper 2, these fabrics are less preferred, because they are not very absorbent and ounces of absorbency potential of the diaper 2 are lost when such fabrics are used.

Preferably, stretchy French terry fabric blends are used for the outer layer 4 of the diaper 2, because of the stretch and trimness of the fabric. Preferably, the inner layer 6 of the diaper 2 is also a stretchy French terry or a stretchy fleece blend. However, as stated herein, different fabric blends offer customizable absorption as needed for small, frequent wetter wearers, or for wearers with fast-flooding absorbency needs. All fabric combinations, for either the outer layer 4 or the inner layer 6, can be modified and adjusted to fit the user's specific absorption needs for the wearer.

Also, in construction of the diaper 2 of the present invention, preferred threads are used to finish or serge the seam allowances 8, 10 of the outer layer 4 and the inner layer 6, respectively, and to attach the outer layer 4 to the inner layer 6 along attachment seam 14. Any high quality serge or overlock thread can be used. A wooly nylon or stretch thread works best and creates a soft hem and allows for ultimate stretch as the user dons or wraps the diaper 2 around the wearer without the threads breaking. Additionally, using a flexible thread will extend the fit of the diaper 2 by providing optimal stretch of the fabric in use.

In use, the stretch of the fabric and thread allow the diaper 2 to be pulled and manipulated by the user in a way to achieve a perfect seal around the legs and stomach of the wearer. The diaper 2 can be stretched to the maximum by the user without fearing seam or fabric failure. Because the fabric can be pulled and manipulated, the user is able to achieve a leg seal on the wearer equivalent to that of a stretchy flat cloth diaper. The leg seal keeps the waste in the diaper 2 and prevents leaking on the waterproof cover of choice, as well as allows for breathable, cover-free wearing time by the wearer without leaks from the legs or back of the diaper 2.

The diaper 2 of the present invention is readily scalable to different sizes as may be needed by different ages and physical sizes of wearers. For example, a size small diaper 2 is suitable for wearers from about 5 pounds to about 15 pounds and has dimensions of about 12.5" in length along the outer layer 4 center line A-A' 16, and about 17.0" in width across the outer layer 4 from an outer edge seam allowance 8 of the left hip wing 20 to an outer edge seam allowance 8 of the right hip wing 22; and 11.0" in length along the inner layer 6 center line B-B' 18, and about 20.0" in width across the inner layer 6 from an outer edge seam allowance 10 of the left absorbency panel 30 to an outer edge seam allowance 20 of the right absorbency panel 32.

For example, a size medium diaper 2 is suitable for wearers from about 10 pounds to about 25 pounds and has dimensions of about 15.0" in length along the outer layer 4 center line A-A' 16, and about 21.0" in width across the outer layer 4 from an outer edge seam allowance 8 of the left hip wing 20 to an outer edge seam allowance 8 of the right hip wing 22; and 13.0" in length along the inner layer 6 center line B-B' 18, and about 24.0" in width across the inner layer 6 from an outer edge seam allowance 10 of the left absorbency panel 30 to an outer edge seam allowance 20 of the right absorbency panel 32.

For example, a size large diaper 2 is suitable for wearers from about 20 pounds to about 35 pounds and has dimensions of about 17.0" in length along the outer layer 4 center line A-A' 16, and about 25.5" in width across the outer layer 4 from an outer edge seam allowance 8 of the left hip wing 20 to an outer edge seam allowance 8 of the right hip wing 22; and 15.0" in length along the inner layer 6 center line B-B' 18, and about 26.0" in width across the inner layer 6 from an outer edge seam allowance 10 of the left absorbency panel 30 to an outer edge seam allowance 20 of the right absorbency panel 32.

For example, a size extra-large diaper 2 is suitable for wearers from about 30 pounds to about 75 pounds and has dimensions of about 19.0" in length along the outer layer 4 center line A-A' 16, and about 27.5" in width across the outer layer 4 from an outer edge seam allowance 8 of the left hip wing 20 to an outer edge seam allowance 8 of the right hip wing 22; and 18.0" in length along the inner layer 6 center line B-B' 18, and about 28.0" in width across the inner layer 6 from an outer edge seam allowance 10 of the left absorbency panel 30 to an outer edge seam allowance 20 of the right absorbency panel 32.

To construct the diaper 2 of the present invention, each of the outer layer 4 and the inner layer 6 are finished with serge or overlock stitching along the respective seam allowances 8, 10. The inner layer 6 is then attached to the outer layer 4 with serge or overlock stitching along the attachment seam 14 of the tab 12. Preferably, when attaching the inner layer 6 to the outer layer 4, the portion of the seam allowance 10 equivalent to the area of an attachment seam 14 of the tab 12 is attached to a corresponding portion of the seam allowance 8 of the outer layer 4 in one sewing pass as one continuous seam. This can be done by first serging the inner layer 6 along seam allowance 10 by starting at a top right corner of the tab 12, then serging along the seam allowance 10 in a clockwise direction, and upon reaching a top left corner of the tab 12, placing the outer layer 4 underneath the inner layer 6, aligning the center lines A-A' 16 and B-B' 18, and then serging is continued through both the inner layer 6 and the outer layer 4 along both seam allowances 8, 10 and along and across attachment seam 14, and then serging is continued on the outer layer 4 along seam allowance 8 in a clockwise direction, and the serging is ended either at a leading edge of, along, or at a following edge of, the attachment seam 14. For a strong and durable attachment seam 14 of the diaper 2 that will hold up during repeated use and laundering, the direction of the fabric grain for inner layer 6 should be aligned with and parallel to center line B-B' 18.

Benefits of attachment seam 14 are that the outer layer 4 and the inner layer 6 of the diaper 2 stay attached during laundering, and allow the layers 4, 6 to flow freely of each other in the washer and dryer, which ensures not only that the diaper 2 gets as clean as possible, but also reduces the length of the wash and dry cycles. Also, during laundering of the diaper 2, water and detergent are able to flow freely through the fabric fibers of the layers 4, 6 avoiding the consistent issues of buildup of mineral or ammonia residues from human waste in the cloth or fabric. Another benefit of the attachment seam 14 is that diaper preparation is cut in half, with an easy to use, grab-and-go diaper 2, because the diaper 2 does not need to be folded or stuffed prior to use upon the wearer. The user can grab the diaper 2 out of the dryer, quickly fold the inner layer 6 into a rectangle, and put the diaper 2 on the wearer. Also, with the inner layer 6 attached to the outer layer 4, the wearer cannot unfold the diaper 2.

Another benefit of the minimal attachment seam 14 is that the inner layer 6 is free moving in relation to the outer layer 4, with the exception of the tab 12 connecting the layers 4, 6 of the diaper together. The minimal attachment seam 14 allows the user to fold the inner layer 6 completely clear of a seal line of the diaper 2 across and against a back of the wearer, and allows the diaper 2 fabric to stretch and manipulate around the wearer's body shape for perfect back and leg seals of the diaper 2 on the wearer every single time with very little effort by the user. Even the user with little cloth diaper experience can easily use the diaper 2 of the present invention.

Figure 5:
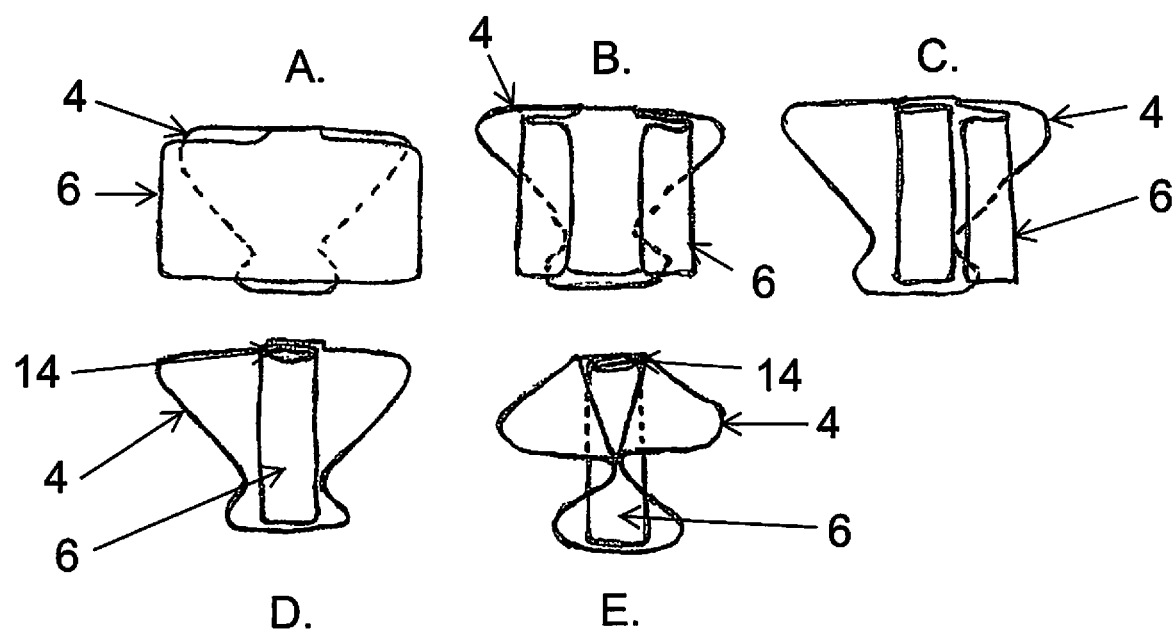
FIG. 5A through FIG. 5E are top plan views of the cloth diaper of the present invention being folded into a configuration for use.

To use the diaper 2 of the present invention with the wearer, the user first lays the diaper 2 flat in an initial folded configuration as show in FIG. 4 and FIG. 5A. Next, the user folds the inner layer 6 into any desired absorbency configuration as suited to the wearer's needs, as shown, for example step-by-step in FIG. 5B through FIG. 5D. In FIG. 5A through FIG. 5C, the dotted line indicates the outer layer 4 beneath the inner layer 6. In FIG. 5E, the dotted line indicates the inner layer 6 beneath the outer layer 4. The user the lays the wearer on top of the folded diaper 2 as shown in FIG. 5D, buttocks side against the diaper 2, and with the wearer's belly button in line with the attachment seam 14. As shown in FIG. 5E, the user also folds each side of the outer layer 4 inward toward center line A-A' 16 from about 0.5" to about 1.5" as needed so that the edges of outer layer 4 are tight up against the wearer's buttocks, and will fit between the wearer's legs. The user then pulls this folded section and stomach panel 24 of the diaper 2 tightly up between the wearer's legs, and places the stomach panel 24 so that it is resting flat across the wearer's hips. While holding the stomach panel 24 in place, the user tightly pulls the right hip wing 22 wing out, up, and then across and flat over the wearer's hips; next the user holds the right hip wing 22 in place over the stomach panel 24, and then repeats the process with the left hip wing 20 (the user tightly pulls the left hip wing 20 wing out, up, and then across and flat over the wearer's hips) and overlaps the left hip wing 20 across and flat over the right hip wing 22. As the user chooses, the order of closing the right hip wing 22 and left hip wing 20 may be reversed. Once the hip wings 20, 22 are in place, the user then secures the diaper 2 on the wearer using what is commonly referred to as the 'Good Key Method' with a diaper fastener of the user's choice. Suitable fasteners are diaper pins, Boingos, Snappis, diaper belt, or the like. With the diaper 2 of the present invention, diapering the wearer by the user is quick and easy, and once the wearer is laid on the diaper, no amount of squirming by the wearer will unfold the shape or folded absorbency of the folded inner layer 6.

Another benefit of the diaper 2 of the present invention is that due to the stretch of the fabric used in the diaper 2, the user does not have to worry about pulling too hard on the diaper 2 while donning the diaper 2 on the wearer. When using the Good Key Method to secure the diaper 2 of the present invention on the wearer, the user can achieve a good leg seal and a separate, outer cover with elastic on the leg and body openings is not needed to keep waste contained in the diaper 2. Although very absorbent, the diaper 2 of the present invention is not waterproof, and a separate waterproof cover is recommended.

Other benefits of the stomach panel 24 are that when the diaper 2 is worn by the wearer, the stomach panel 24 sits right where the wearer's legs meet the hips. When the stomach panel 24 is in place, it also adds extra layers of fabric over the wearer's stomach area under the belly button and over each hip bone adding protection from diaper fasteners. The stomach panel 24 also serves to keep a front of the diaper 2 from drooping while worn by the wearer, and adds extra absorption in the front of the diaper 2.

Other benefits of the diaper 2 of the present invention are that the tab 12 of the inner layer 6 may be turned by the user downward and into the inside of the diaper 2, thus allowing from about 0.25" to about 0.5" of fabric to be rolled into the back of the diaper 2 to achieve a good seal against the wearer's back when the diaper 2 is worn. The shape of the outer layer 4 of the diaper 2, and use of a stretch fabric for the outer layer 4, allows the user to roll and stretch the fabric of the diaper 2 at the legs, hips, and waist of the wearer, and ensures the best back seal and leg seal possible, keeping waste in the diaper 2 and not on the wearer's clothing. Additionally, because there is no unneeded or excess fabric for the outer layer 4, and the inner layer 6 can be folded away from the wearer's leg seal line, the diaper 2 is very trim, and has bulk only and exactly where needed for waster absorbency.

Unless defined otherwise, all technical and scientific terms used herein have the same meaning as commonly understood by one of ordinary skill in the art to which this invention belongs. Although the present invention has been described with reference to specific embodiments, and to preferred methods and materials, it is understood that any methods and materials similar or equivalent to those described herein can also be used in the practice or testing of the present invention, and that modifications and variations of the present invention are possible without departing from the scope of the invention, which is defined by the claims set forth below.

The invention claimed is:

1. A cloth diaper comprising:
   an outer layer having a main panel with a trapezoid shape with a left hip wing and a right hip wing, which hip wings are contiguous with each other, and having a stomach panel with an ellipse shape with a left stomach wing and a right stomach wing, which stomach wings are contiguous with each other, and the main panel is contiguous along a shorter width of the trapezoid shape with the stomach panel; and
   an inner layer having a rectangle shape with a left absorbency panel and a right absorbency panel, which panels are contiguous with each other, and having a tab with an area above a tab line, the inner layer having a bottom edge that travels a length of the left absorbency panel and the right absorbency panel and an attachment seam;
   an attachment seam connecting the tab to the outer layer;

wherein the tab extends a partial length of the bottom edge such that a majority of the left absorbency panel is not connected to the tab or the outer layer and a majority of the right absorbency panel is not connected to the tab or the outer layer;

wherein a length of the bottom edge of the inner layer is equal to or greater than a width of the outer layer;

wherein the inner layer is configured to fold into a plurality of absorbency configurations before the inner layer and the outer layer are folded together along the attachment seam;

wherein the tab of the inner layer is attached along the attachment seam to a corresponding portion of the outer layer;

wherein the outer layer comprises an outer layer seam allowance which binds a perimeter of the outer layer, and the inner layer comprises an inner layer seam allowance which binds a perimeter of the inner layer;

wherein the outer layer comprises at least a layer of fabric finished along the seam allowance;

wherein the inner layer comprises at least a layer of fabric finished along the seam allowance;

wherein a direction of a fabric grain for the inner layer is aligned with and parallel to a center line of the inner layer; and wherein the outer layer and the inner layer are constructed of a fabric having from about 3% to about 7% of synthetic, elastic fiber content, and the fabric used to construct the diaper is selected from the group consisting of stretch French terry, stretch fleece, and blends thereof, and the fabric is made of fibers selected from the group consisting of bamboo, cotton, organic cotton, hemp, soy, wool, Merino wool, lyocell, modal, and blends thereof.

\* \* \* \* \*